United States Patent [19]

Davis, deceased et al.

[11] 4,449,005
[45] May 15, 1984

[54] DEHYDROHALOGENATION PROCESS

[75] Inventors: George T. Davis, deceased, late of Bel Air, Md., by Maureen A. Davis, administratrix; William R. Hydro, Bel Air, Md.

[73] Assignee: The United States of America as represented by the Secretary of the Army, Washington, D.C.

[21] Appl. No.: 405,680

[22] Filed: Aug. 6, 1982

[51] Int. Cl.$^3$ .................................. C07C 149/10
[52] U.S. Cl. ........................... 568/59; 568/60
[58] Field of Search ............... 568/21, 25, 38, 59, 568/60

[56] References Cited

U.S. PATENT DOCUMENTS 2,796,437 6/1957 Park .................................. 568/21

FOREIGN PATENT DOCUMENTS 1298986 7/1969 Fed. Rep. of Germany .

OTHER PUBLICATIONS

Chem. Rev. (1980) 80,429–452, Fluoride Ion as a Base in Organic Synthesis, James H. Clark.
Tetrahedron Letters No. 31,2727–28 (1970), The Novel Orientation in the Fluoride Promoted Elimination Reactions, J. Hayami et al.
Tetrahedron Letters No. 11,1385–86 (1968), Quaternary Ammonium Fluoride, A Reagent for Proton Abstraction, J. Hayami et al.
J. Org. Chem. 35, No. 4,1023–25 (1970), Eliminations from 2-Butyl Halides Induced by Halide Ions in DMR and DMSO, R. A. Bartsch.
J. Chem. Soc. Perkin Trans. 1,340–343 (1974), Use of Fluoride Ion as a Reagent in Acetylene–and Allene-Forming Eliminations, F. Naso et al.
Chemical Aabstracts 76,24604 (1972), Reactions of Tetraethylammonium Fluoride, Hayami, et al.
Bull. Chem. Soc. Japan 44,1628–32 (1971), Elimination Reactions Promoted by Fluoride Ion in Acetonitrile, Elimination Reaction from 2-Arylethyl Derivatives, J. Hayami, et al.
Chemical Abstracts 73,44676m (1970), Metal Fluorides for Dehydrofluorination, Dehydrofluorination of 1,1-Difluorethane over Metal Fluorides, Okazaki, et al.
Bull. Chem. Soc. Japan 44,1369–72 (1971), The Elimination Orientation in The Fluoride-Promoted Olefin Formation, N. Ono.
Tetrahedron Letters, No. 4,297–298 (1970), Stereochemistry of Base-Catalyzed Eliminations from 2-Alkyl Bromides, R. A. Bartsch.
J. Am Chem. Soc. 82, 3091–98, Substitution and Addition Reactions of the Fluoroolefins, IV Reactions of Fluoride Ion with Fluoroolefins, W. T. Miller, et al.
Tetrahedron Letters, No. 44,4571–74 (1972), On the Mechanism of Phase Transfer Catalysis, A. W. Herriott, et al.
Chem. Abstracts, 95:42333c, 1,2,3-Trihalo-2-Butenes, R. Kazaryan, et al.

*Primary Examiner*—Donald G. Daus
*Assistant Examiner*—M. C. Eakin
*Attorney, Agent, or Firm*—Robert P. Gibson; Anthony T. Lane; A. Victor Erkkila

[57] ABSTRACT

Aliphatic and cycloaliphatic halogen compounds containing a halogen atom and a hydrogen atom attached to adjacent carbon atoms are dehydrohalogenated to the corresponding unsaturated compounds by contact with a quaternary ammonium fluoride or quaternary phosphonium fluoride.

8 Claims, No Drawings

DEHYDROHALOGENATION PROCESS

GOVERNMENTAL INTEREST

The invention described herein may be manufactured, used, and licensed by or for the Government for governmental purposes without the payment to us of any royalties thereon.

BACKGROUND OF THE INVENTION

Mustard gas [bis(2-chloroethyl)sulfide, b.p. 215° C.] cannot be detected with high sensitivity by means of ion cluster ionization detectors. However, this problem can be overcome by dehydrochlorinating the mustard gas to divinyl sulfide (b.p. 85° C.) and oxidizing the latter to divinyl sulfoxide, b.p. 81° C. at 16 mm which exhibits high sensitivity by ion cluster ionization detectors.

Accordingly, it is an object of the present invention to provide a process for dehydrochlorinating mustard gas to divinyl sulfide.

Another object of the invention is to provide a novel process for dehydrohalogenating aliphatic and cycloaliphatic halides to the corresponding unsaturated compounds.

Other objects and advantages of the invention will become apparent from the following description.

SUMMARY OF THE INVENTION

In accordance with the process of the present invention 2-chloroethyl sulfides and, in general, aliphatic and cycloaliphatic halogen compounds, which contain a halogen atom and a hydrogen atom attached to adjacent carbon atoms so as to be amenable to dehydrohalogenation, are rapidly and efficiently dehydrohalogenated to produce the corresponding unsaturated compounds by contacting the halogen compound with a quaternary compound selected from the group consisting of quaternary ammonium fluorides and quaternary phosphonium fluorides at a temperature and for a period of time sufficient to effect dehydrohalogenation to the corresponding unsaturated compounds.

The process of the present invention provides an important technical advance in the art in that it effects rapid and efficient dehydrohalogenation of such halogen compounds to the corresponding unsaturated compounds.

DETAILED DESCRIPTION OF THE INVENTION

Any aliphatic or cycloaliphatic halogen compound, which contains a halogen atom and a hydrogen atom attached to adjacent (alpha and beta) carbon atoms such that it can be dehydrohalogenated to the corresponding unsaturated compound, e.g., 1-chlorobutane→1-butene, as is well known in the art, can be employed as starting material in the process of the present invention. The halogen atom may be chlorine, bromine, iodine or fluorine.

Preferred halogen compound starting materials include alkyl and cycloalkyl halides, particularly chlorides, wherein the alkyl and cycloalkyl groups may contain additional substituents, including halogen, alkoxy, alkylthio, and aryl. Particularly preferred starting materials are represented by the formula

$$R-(S)_n-CH_2-CH_2-Cl$$

wherein R is alkyl, chloroalkyl, and aryl and n is 0 or 1. Examples of suitable halogen compound starting materials include ethyl chloride, 1-chlorobutane, 3-bromo-3-methylpentane, 1-iododecane, 1,6-dichlorohexane, chlorocyclohexane, β-chloroethylbenzene, 1-fluoropropane, 1-bromodecane, bromocyclohexane, 2-chloroethyl methylsulfide, 2-chloroethyl-n-dodecyl sulfide, 2-chloroethyl benzyl sulfide, 2-chloroethylphenyl sulfide, 2-bromoethyl n-hexyl sulfide, bis(2-chloroethyl)sulfide and bis(2-bromoethyl)sulfide.

Quaternary ammonium and phosphonium fluorides which can be suitably employed in the process of the present invention include tetraalkylammonium fluorides, e.g., tetramethylammonium fluoride, tetraethylammonium fluoride, tetrabutylammonium fluoride, and trimethylbenzylammonium fluoride, methylpyridinium fluoride, laurylpyridium fluoride, dimethylmorpholinium fluoride, tetramethylphosphonium fluoride, and tetraphenylphosphonium fluoride. Such compounds are represented by the following general formula:

wherein F is fluorine, X is nitrogen or phosphorus, and R represents the same or different monovalent organic radicals or 2 or 3Rs together with X form a heterocyclic radical containing the nitrogen or phosphorus atom as a ring member, as in pyridine. These fluorides can be prepared in known manner by neutralizing the corresponding strongly basic quaternary ammonium and phosphonium hydroxides of the formula

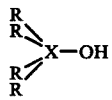

wherein R and X have the foregoing definitions, with hydrofluoric acid.

The quaternary compound appears to function as a catalyst for the dehydrohalogenation reaction, enabling the reaction to be accomplished rapidly at moderate temperatures. The amount of quaternary compound is not critical and may vary widely. Generally within limits, the reaction is promoted by increasing the ratio of quaternary compound to halogen compound to be dehydrohalogenated. The amount of quaternary compound employed will vary depending on the particular halogen compound starting material as well as other reaction conditions employed, such as temperature.

The dehydrohalogenation reaction may be carried out by contacting the halogen compound starting material with the quaternary compound in any suitable manner, e.g., dissolved or suspended in a liquid solvent or diluent, at a temperature and for a period of time to effect the dehydrohalogenation reaction. For example, the halogen compound may be dissolved in a liquid solvent, if necessary, and vaporized in a stream of carrier gas, e.g., nitrogen, and the vapors contacted with the quaternary compound, preferably coated or supported on a solid substrate, e.g., pieces of glass, ceramic or silica gel.

Temperatures which can be employed for carrying out the reaction or for producing optimum yields may depend on the particular halogen compound, quaternary fluoride and other reaction conditions employed, and can be readily determined by those skilled in the art. The rate of the dehydrohalogenation reaction is generally accelerated by increasing the reaction temperature. The reaction rate at room temperature is generally unduly slow so that higher temperatures of at least about 40° C., preferably between about 45° C. and 80° C., are employed. At elevated temperatures, e.g., of about 80° C., the dehydrogenation reaction in some cases can be effected in a few minutes or less with essentially quantitative conversion of halogen compound to corresponding unsaturated compound.

The presence of water, particularly in the quaternary fluoride compound, has an adverse effect on the dehydrohalogenation reaction. Accordingly, for optimum results the reaction is carried out while minimizing the presence of water, preferably under anhydrous conditions.

The following examples serve to illustrate specific embodiments of the method of carrying out the process of the present invention.

The apparatus and general procedure employed in the examples are described below.

A three-necked, horizontal, cylindrically shaped vessel, referred to as the "saturator", containing an open-ended fritted glass cylinder placed therein, was equipped with a thermometer, nitrogen gas inlet and a vertical glass column (2 cm dia. × 40 cm. long). The column was provided with a thermometer and packed with glass helices coated with quaternary ammonium (or phosphonium) fluoride. The vessel and column were heated separately. The outlet at the top of the column was connected by a glass tube to a test tube immersed in a cooling bath consisting of a dry ice-acetone mixture. In operation, the saturator was half-filled with the halogen compound and nitrogen gas was then passed over the halogen compound in the saturator, thereby carrying the vapors of the halogen compound through the column containing the glass helices coated with the quaternary fluoride compound. The reaction products from the column were condensed and collected in the dry ice-acetone trap. The volume of exited gas from the trap was measured by displacement of water from an inverted graduated cylinder. The material collected in the trap was taken up in 0.4 ml of carbon tetrachloride and transferred to an NMR tube for analysis.

EXAMPLE 1

A. Preparation of Tetra n-Butylammonium Fluoride, (n-$C_4H_9$)$_4$NF

Tetra n-butylammonium hydroxide (100 ml, marketed by Aldrich Chemical Co.) was neutralized to pH 7.8 with 48% hydrofluoric acid, and the resulting solution was evaporated in vacuo on a rotating film evaporator while maintaining a bath temperature below 40° C. Acetonitrile was added and the evaporation was continued in vacuo at below 40° C. Drying was completed in an evacuated desiccator over phosphorus pentoxide at ambient temperature.

B. Dehydrohalogenation of 2-Chloroethyl Ethyl Sulfide with (n-$C_4H_9$)$_4$NF 88 grams of ⅛ in. glass helices placed in an evaporation dish were covered with a solution prepared by dissolving 6.6 grams of the tetrabutylammonium fluoride obtained in Part A in acetonitrile. The mixture was placed in an oven heated to 38° C., the solvent was removed by evaporation, and 54.2 grams of the coated glass helices were then transferred to the column. The experimental conditions and results are shown in Table 1. The results show that a stoichiometric recovery and 100% conversion of 2-chloroethyl ethyl sulfide to ethyl vinyl sulfide was obtained.

TABLE 1

2-Chloroethyl Ethyl Sulfide Dehydrohalogenation With ($C_4H_9$)$_4$NF
Exit flow rate: 32 ml/min
Unpacked column volume: 100 ml
Helice volume: 25 ml

| Run No. | Temperature Saturator | Column | Time | NMR Analysis (mole %) vinyl* | fluoride** | Bu$_3$N | CH$_3$CN |
|---|---|---|---|---|---|---|---|
| 1 | 25° C. | 80° C. | 3½ hrs | 51*** | none | 7 | 42 |
| 2 | 25 | 80 | 6¾ hrs | 91 | none | 9 | — |
| 3 | 58 | 78 | 5 min | only vinyl observed ~ 10 mg | | | |
| 4 | 58 | 78 | 5 min | only vinyl observed ~ 10 mg | | | |
| 5 | 56 | 80 | 15 min | only vinyl observed ~ 25 mg | | | |
| 6 | 56 | 80 | 15 min | only vinyl observed ~ 25 mg | | | |

*ethyl vinyl sulfide
**2-fluoroethyl ethyl sulfide
***The lower percentage of vinyl detected is attributed mainly to the presence of acetonitrile on the freshly prepared support material.

By employing bis(2-chloroethyl)sulfide in place of 2-chloroethyl ethyl sulfide under the foregoing conditions, divinyl sulfide was obtained in high yields.

EXAMPLE 2

Dehydrohalogenation of 2-Chloroethyl Ethyl Sulfide with ($C_2H_5$)$_4$NF.x$H_2$O The column was charged with 56.4 grams of ⅛ in. glass helices coated with 6.6 wt.% of tetraethylammonium fluoride. The experimental procedure was similar to that described in Example 1. The experimental conditions and results are shown in Table 2. The ($C_2H_5$)$_4$NF.x$H_2$O contained an unknown amount of moisture. The relatively low yield of vinyl compound is attributed to the presence of moisture in the dehydrohalogenating agent which adversely affects the reaction.

TABLE 2

2-Chloroethyl Ethyl Sulfide Dehydrohalogenation with Et$_4$NF.x$H_2$O
Exit flow rate: 32 ml/min

| Run No. | Temperature Saturator | Column | Time | NMR Analysis (mole %) vinyl* | fluoride** | other |
|---|---|---|---|---|---|---|
| 1 | 60° C. | 81° C. | 30 min | 23 | 55 | 23 |
| 2 | 60 | 81 | 15 min | 41 | 41 | 18 |
| 3 | 60 | 81 | 5 min | trace | trace | — |

*ethyl vinyl sulfide
**2-fluoroethyl ethyl sulfide

EXAMPLE 3

A. Preparation of Tetraphenylphosphonium Fluoride ($C_6H_5$)$_4$PF

A solution of 80.9 g (0.476 mole) of silver nitrate in 200 ml of water was added to an agitated solution of 38.1 g (0.925 mole) of sodium hydroxide in 200 ml of water. The resulting brown precipitate of silver oxide hydrate was separated by filtration, washed copiously with water and dried in vacuo.

The silver oxide filter cake thus obtained was suspended in 200 ml of acetonitrile and mixed with a solution of 100 g (0.238 mole) of tetraphenylphosphonium bromide (marketed by Alfa Products Co.) in 200 ml of acetonitrile, thereby forming tetraphenylphosphonium hydroxide and a precipitate of silver bromide, which was then separated by filtration. Hydrofluoric acid was added to the tetraphenylphosphonium hydroxide solution until a pH of 7.2 was obtained, and the resulting mixture was heated in a rotary film evaporator to remove the solvent and dried in a vacuum oven heated to about 40° C. A yield of 73.7 g (corresponding to 86.6% of theory) of tetraphenylphosphonium fluoride was obtained as a solid.

Analysis: Calculated for $(C_6H_5)_4PF$: F 5.30; Found: F 5.24.

B. Dehydrohalogenation of 2-Chloroethyl Ethyl Sulfide with $(C_6H_5)_4PF$

Glass helices were coated with $(C_6H_5)_4PF$ as follows:

A solution of 3.7 grams of $(C_6H_5)_4PF$ obtained in Part A in 75 ml of acetonitrile was mixed with a solution of 0.4 gram of Carbowax 4000 in 75 ml of acetonitrile, and the resulting mixture was poured over 58.3 grams of 1/16 in. glass helices. The solvent was then removed by evaporation in an oven maintained at 38° C., and the total amount of coated glass helices thus obtained was charged to the column. The experimental conditions and results are shown in Table 3.

TABLE 3

2-Chloroethyl Ethyl Sulfide Dehydrohalogenation with a Mixture of 90% $(C_6H_5)_4PF$ and 10% Carbowax 4000

Time: all 30 min
Exit flow rate: 32 ml/min

| Run No. | Temperature Saturator | Column | NMR Analysis (mole %) vinyl* | fluoride** | chloride*** |
|---|---|---|---|---|---|
| 1 | 58° C. | 65° C. | very dilute; only chloride observed | | |
| 2 | 60 | 86 | 29 | 12 | 59 |
| 3 | 60 | 87 | 52 | 10 | 38 |
| 4 | 60 | 87 | 45 | trace | 55 |

TABLE 3-continued

2-Chloroethyl Ethyl Sulfide Dehydrohalogenation with a Mixture of 90% $(C_6H_5)_4PF$ and 10% Carbowax 4000

Time: all 30 min
Exit flow rate: 32 ml/min

| Run No. | Temperature Saturator | Column | NMR Analysis (mole %) vinyl* | fluoride** | chloride*** |
|---|---|---|---|---|---|
| 5 | 63 | 98 | 40 | 14 | 45 |
| 6 | 63 | 98 | 39 | — | 61 |
| 7 | 65 | 120 | 59 | — | 41 |
| 8 | 63 | 61 | 36 | 8 | 56 |

*ethyl vinyl sulfide
**2-fluoroethyl ethyl sulfide
***2-chloroethyl ethyl sulfide The foregoing disclosure is merely illustrative of the principles of this invention and is not to be interpreted in a limiting sense. We wish it to be understood that we do not desire to be limited to the exact details of construction shown and described, because obvious modifications will occur to a person skilled in the art.

We claim:

1. A process for dehydrochlorinating a compound selected from the group consisting of 2-chloroethyl ethyl sulfide and bis(2-chloroethyl)sulfide, which consists essentially of contacting said compound in vapor phase with a quaternary ammonium—or quaternary phosphonium fluoride of the formula $(R)_4 X F$, wherein the R's represent the same or different alkyl radicals containing 1–12 carbon atoms or phenyl, X is nitrogen or phosphorus and F is fluorine, in the absence of a solvent at a temperature and for a period of time sufficient to effect the dehydrochlorination to the corresponding vinyl compound.

2. The process of claim 1, wherein X is nitrogen and R is an alkyl radical of 1 to 12 carbon atoms.

3. The process of claim 1, wherein the fluoride is supported on a solid substrate.

4. The process of claim 1, wherein the chlorethyl compound is vaporized in a stream of inert carrier gas.

5. The process of claim 1, wherein the fluoride is tetraethylammonium fluoride.

6. The process of claim 1, wherein the fluoride is tetra-n-butylammonium fluoride.

7. The process of claim 1, wherein the fluoride is tetraphenylphosphonium fluoride.

8. The process of claim 1 which is carried out at a temperature from about 40° C. to about 120° C.

* * * * *

UNITED STATES PATENT AND TRADEMARK OFFICE
CERTIFICATE OF CORRECTION

PATENT NO. : 4449005
DATED : 5/15/84
INVENTOR(S) : Davis, George T., deceased; late of Bel Air, Md. by Davis,
Maureen A.,administratrix; and Hydro, William R.; Bel Air, Md.

It is certified that error appears in the above—identified patent and that said Letters Patent is hereby corrected as shown below:

On the title page

INVENTOR(S): William R. Hydro, Bel Air, Md. and George T. Davis, deceased; late of Bel Air, Md.

Signed and Sealed this

Twenty-sixth Day of February 1985

[SEAL]

Attest:

DONALD J. QUIGG

Attesting Officer

Acting Commissioner of Patents and Trademarks